Figure 1:
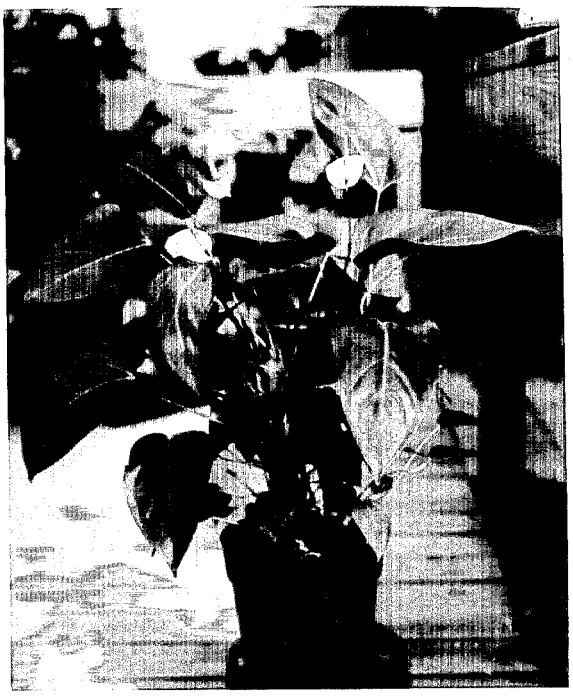

US00PP08131P

United States Patent [19]

Georgusis

[11] Patent Number: Plant 8,131

[45] Date of Patent: Feb. 2, 1993

[54] ANTHURIUM 'GEORGUSIS PINK NUMBER 1'

[75] Inventor: James J. Georgusis, Hilo, Hi.

[73] Assignee: Oglesby Plant Laboratories Inc., Altha, Fla.

[21] Appl. No.: 740,498

[22] Filed: Aug. 5, 1991

[51] Int. Cl.[5] ..... A01H 5/00

[52] U.S. Cl. ..... Plt./88.1

[58] Field of Search ..... Plt./88.1

*Primary Examiner*—James R. Feyrer

*Attorney, Agent, or Firm*—Frank B. Robb

[57] ABSTRACT

A compact freely branching and flowering Anthurium hybrid with light pink flower color unevenly dispersed over a white background, with contrasting dark green leaves providing a flowering, commercial pot plant of distinct appearance.

1 Drawing Sheet

GENERAL DESCRIPTION OF THE INVENTION

This invention relates to an Anthurium cultivar which was selected from a planting of Anthurium because it appeared to offer a quite different overall appearance because of the flower color which was rather unusual.

The cultivar herein described was in fact selected because of the delicate pink general appearance of the flowers which is in decided contrast to the dark green foliage. The pink color was rather unevenly dispersed over the white background.

The contrast between the pink flower color and the dark green leaves makes the plant well suited as a commercial pot plant.

In addition, greenhouse trials in the vicinity of Altha, Fla. indicate that the cultivar has good resistance against traditional diseases which affect Anthurium plants and no unusual susceptibility to insects has been found to be present up to the present time.

The foregoing is of interest because the cultivar was selected from the planting which was made in the vicinity of Hollywood, Fla.

Adverting to the flower color, as might be expected, the color initially makes its appearance as unevenly dispersed red-purple over the white background, with the color becoming somewhat more pronounced as the flowers mature. Actually the color becomes more distinct as the blooms age, but it never attains any deep pink color.

More specifically, the red-purple appears upon close examination as being irregularly dispersed over the white background.

In view of the foregoing, the cultivar is denominated as Anthurium Georgusis Pink #1 as a suitable designation.

I have caused the cultivar to be asexually reproduced and found that the characteristics hereinafter described in detail, come true in successive generations which have been reproduced by tissue culture in the vicinity of Altha, Fla.

Since the initial plant selected was grown in a cultivated area, in which a number of Anthurium plants have been grown, the cultivar hereof may be compared as set forth hereinafter with some of those plants which were grown under similar conditions in the Altha, Fla. area.

In the drawing showing the plant hereof,

FIG. 1 discloses a typical plant with the rather delicate pink flowers contrasted with the dark green leaves.

Figure 2:
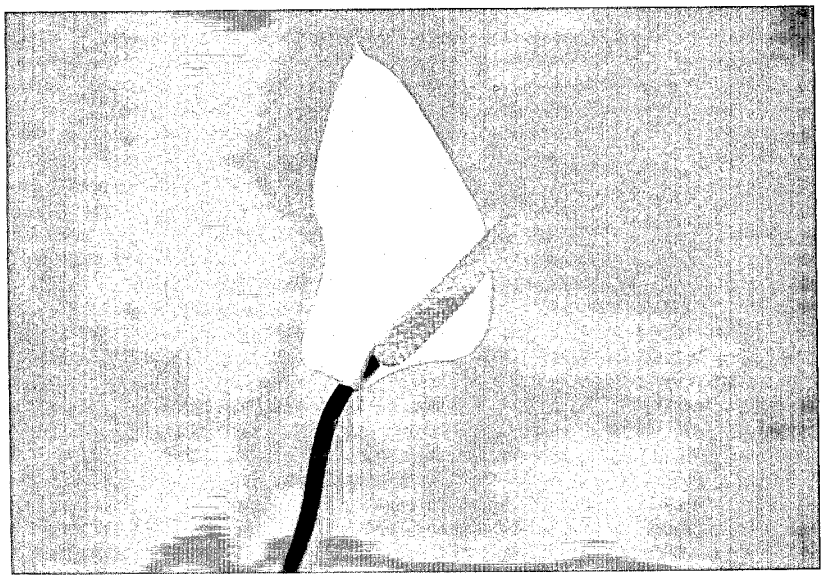

In FIG. 2, a single flower is shown.

In order to clearly define many of the characteristics of the new cultivar, the following description is set forth:

Parentage:

*Seed parent.*—*Anthurium* × *cultorum.*

*Pollen parent.*—*Anthurium antioquiense.*

Propagation: Plant tissue culture.

Plant descriptions: All colors are described using The Royal Horticultural Society Colour Chart. Measurements and colors were taken from mature plants grown near Altha, Fla.

*Stem.*—Smooth, yellow-green (144 D).

*Lenticels.*—Not obvious.

*Petioles.*—32–37 cm. Smooth. Color when young, yellow-green (146 C). Mature, yellow-green (146 B).

*Leaves.*—Ovate, cuspidate tip. Leaf bases change with overall plant maturity. Leaves formed on young plants have an obtuse base eventually of isolated leaf is of mature leaf). A mature leaf ranges from 18–22 cm long by 11–13 cm wide, depending on age. Reflexed. Margins entire.

*Color.*—Young expanding leaf, green (143 A) adaxial (top), polished, abaxial (bottom) yellow-green (146 D). Mature leaf, green (137 A) adaxial (top), yellow-green (146 C) abaxial (bottom). Dull appearance.

*Veins.*—Main vein (Rib) prominent from base of leaf to mid section of leaf. Both main rib and lateral veins near base of leaf protrude from leaf surface. Rib and veins in remainder of leaf are even to somewhat sunken in the leaf surface. The rib color is in sharp contrast to the leaf color. On a young leaf, the rib color near the base of the leaf is yellow-green (146 C) changing towards the leaf tip to green (143 A). On a mature leaf the rib color is yellow-green (146 B) near the base changing towards the tip to green (137 A).

*Leaf sheath.*—10–11 cm long pending age. Surrounds young leaf during early developmental stages and is directly attached to the stem below the leaf attachment. The leaf sheath surrounding the youngest leaf is yellow-green (144 D). With age turns greyed-orange (165 B).

Flower:

*Type.*—Spathe and spadix. Spathe tightly rolled around spadix during development. The spathe is fully opened when peduncle is fully elongated. The spathe is smooth, unpuckered, ovate, obtuse base, cuspidate tip. Typically, a width to length ratio 5.5–6 cm by 3.5–4.5 cm wide. Polished appearance. Flowers are consistently held above the foliage.

*Spathe color.*—Flower color pigment is irregularly dispersed as red-purple (65 A-B) over a background of white (155 D). As a young flower, the red-purple of pigmentation is more concentrated towards the margins of the spathe while the area around the mid vein is predominantly white. The red-purple pigmentation is more evenly distributed as the flower matures. The red-purple color is more prominent under cooler conditions.

*Spathe veins.*—Inconspicuous. Protrude from spathe surface.

*Peduncle.*—40–42 cm long. Yellow-green (146 C) at maturity.

Reproductive organs:

*Spadix.*—4–5 cm long, 7–8 mm wide at base. A young spadix color changes from the base of the spadix, red-purple (68 C) to the middle section, red-purple (73 C) to the tip, red-purple (64 A). Mature spadix, base red (55 B) blending to tip red purple (61 B).

*Stamens.*—Anthers and filaments not clearly visible.

Flowering time: After approximately 7–10 months depending on season 1–4 blossoms will be present. Smaller flowers may occur on less mature plants.

Roots: Root developed above soil line are fleshy and non-branching. Roots developed below the soil line are fleshy and well branched with fine lateral roots.

Diseases: Initial greenhouse trials in Altha, Fla. indicate good resistance against traditional diseases.

Insects: No unusual susceptibility to insects noted to date.

COMPARISON WITH KNOWN VARIETIES

Note: These comparisons were made from plants grown under similar conditions near Altha, Fla.

Anthurium 'Rosa': Rosa is a larger plant with a somewhat loose spreading growth habit. The leaves are a lighter green with the newest leaves a bronze color. Rosa displays larger, heart shaped, puckered, red (48 D) flowers.

Anthurium 'Ozaki Red': Tall, leggy growth habit. Exhibits less lateral branching. Leaves generally lighter green color. Flower is heart shaped, puckered, red (47 A-B).

Anthurium 'Lady Jane': Similar in growth habit, leaf shape and color. Flowers wider and longer (1:2 ratio), smooth, red (51 B). Flowers produced on young plants open even to or slightly below foliage canopy.

Anthurium 'Southern Blush': Similar in size with a loose spreading habit. Leaves are lighter green with the new growth a bronze color. Leaf blade thinner and narrower. Leaves are held on longer petioles. The same size flower is displayed above the foliage. The flower is heart shaped, smooth, red (54 B-C), with darker margins.

I claim:

1. A new and distinct Anthurium cultivar substantially as herein shown and described characterized particularly as to novelty by the red-purple flower color pigment irregularly dispersed over the white background becoming more evenly distributed as the flower matures, the freely branching and flowering form of the plant, dark green leaves contrasting with light pink flower color, and the substantially for commercial distribution as a flowering pot plant.

* * * * *